(12) United States Patent
Wu et al.

(10) Patent No.: US 11,033,644 B2
(45) Date of Patent: *Jun. 15, 2021

(54) UV STERILIZATION DEVICE

(71) Applicant: Purity (Xiamen) Sanitary Ware Co., Ltd., Xiamen (CN)

(72) Inventors: James Wu, Taichung (TW); Alex Wu, Taichung (TW); Ce-Wen Yang, Xiamen (CN)

(73) Assignee: PURITY (XIAMEN) SANITARY WARE CO., LTD., Xiamen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/879,924

(22) Filed: May 21, 2020

(65) Prior Publication Data

US 2020/0339441 A1     Oct. 29, 2020

Related U.S. Application Data

(63) Continuation-in-part of application No. 16/391,695, filed on Apr. 23, 2019, now Pat. No. 10,662,078.

(51) Int. Cl.
*A61L 2/10* (2006.01)
*C02F 1/32* (2006.01)

(52) U.S. Cl.
CPC .............. *A61L 2/10* (2013.01); *C02F 1/325* (2013.01); *C02F 2201/004* (2013.01); *C02F 2201/005* (2013.01); *C02F 2201/009* (2013.01); *C02F 2201/3228* (2013.01)

(58) Field of Classification Search
CPC .............. C02F 1/32; C02F 2201/3222; C02F 2201/328; C02F 2303/04; C02F 1/325; C02F 2201/004; C02F 2201/005; C02F 2201/009; A61L 2/10
USPC ........... 250/435, 436, 453.11, 454.11, 504 R
See application file for complete search history.

(56) References Cited

U.S. PATENT DOCUMENTS

| 7,270,748 B1* | 9/2007 | Lieggi | C02F 1/325 210/198.1 |
| 10,662,078 B1* | 5/2020 | Wu | C02F 1/32 |
| 2005/0077732 A1* | 4/2005 | Baarman | C02F 1/325 290/54 |
| 2006/0131246 A1* | 6/2006 | Ehlers, Sr. | C02F 1/325 210/748.1 |
| 2009/0026385 A1* | 1/2009 | Knight | A61L 2/10 250/432 R |

(Continued)

*Primary Examiner* — Nicole M Ippolito
(74) *Attorney, Agent, or Firm* — Birch, Stewart, Kolasch & Birch, LLP

(57) ABSTRACT

A UV sterilization device includes a body, a power module and a UV sterilization assembly. The body includes a housing, an inlet end and an outlet end, wherein the inlet end and the outlet end are positioned on the housing and communicate with the housing; the inlet end and an outlet end communicate with each other through the housing. The power module is positioned on the body for supply electric power. The UV sterilization assembly is positioned on the body, and electrically connected to the power module; the UV sterilization assembly includes a UV source and at least one reflector, wherein the UV source could emit UV light to the at least one reflector, and the UV source and the at least one reflector are positioned around a sterilization channel, the sterilization channel communicates with the inlet end and the outlet end of the body.

12 Claims, 12 Drawing Sheets

(56) References Cited

U.S. PATENT DOCUMENTS

2015/0359915 A1* 12/2015 Farren .................. A61L 2/24
　　　　　　　　　　　　　　　　　　　　　　422/24
2017/0088440 A1* 3/2017 Lin ..................... C02F 1/325

* cited by examiner

UV STERILIZATION DEVICE

CROSS-REFERENCE TO RELATED APPLICATIONS

This application is a Continuation-in-Part of copending application Ser. No. 16/391,695, filed on Apr. 23, 2019, which is hereby expressly incorporated by reference into the present application.

BACKGROUND OF THE INVENTION

1. Technical Field

The present disclosure relates generally to a UV sterilization device, and more particularly to a UV sterilization device to provide sterilized water.

2. Description of Related Art

With the advancement of society and industry, people's requirements for quality of life are getting higher and higher.

As far as the quality of water used in daily life is concerned, whether it is bathing water, washing water for fruits and vegetables, or drinking water, users often connect tap water to water filtering equipment to remove bacteria, impurities and pollutants. However, there may still be many bacteria or viruses in the filtered water flowing out of the water filtering equipment, and generally, the filtered water cannot be directly consumed. The filtered water needs to be further boiled in order to be completely sterilized.

In recent years, a UV sterilization equipment that can be connected in series with a water filtration equipment has appeared on the market. With the UV sterilizing equipment, the filtered water flowing out of the water filtering equipment can be further thoroughly sterilized and disinfected. However, the conventional UV sterilization equipment needs external power supply and is bulky, so that it needs to install the conventional UV sterilization equipment close to the socket, and needs to make an enough space to install the conventional UV sterilization equipment.

At least for the above reasons, the conventional UV sterilization device still have room for improvements.

BRIEF SUMMARY OF THE INVENTION

In view of the above, the primary objective of the present disclosure is to provide a UV sterilization device which has a slim size and does not need external power supply, so that the UV sterilization device is convenient to use.

The present disclosure provides a UV sterilization device includes a body, a power module and a UV sterilization assembly. The body includes a housing, an inlet end and an outlet end, wherein the inlet end and the outlet end are positioned on the housing and communicate with the housing; the inlet end and an outlet end communicate with each other through the housing. The power module is positioned on the body for supply electric power. The UV sterilization assembly is positioned on the body, and electrically connected to the power module; the UV sterilization assembly includes a UV source and at least one reflector, wherein the UV source could emit UV light to the at least one reflector, and the UV source and the at least one reflector are positioned around a sterilization channel, the sterilization channel communicates with the inlet end and the outlet end of the body.

With the aforementioned design, the UV sterilization device includes a power module which could supply electric power, whereby to provide the electric power to the UV sterilization assembly. Thereby, the UV sterilization device provided in the present invention has a slim size, so that there is no need to make an enough space to install the UV sterilization device.

BRIEF DESCRIPTION OF THE SEVERAL VIEWS OF THE DRAWINGS

The present disclosure will be best understood by referring to the following detailed description of some illustrative embodiments in conjunction with the accompanying drawings, in which.

DETAILED DESCRIPTION OF THE INVENTION

Figure 1:
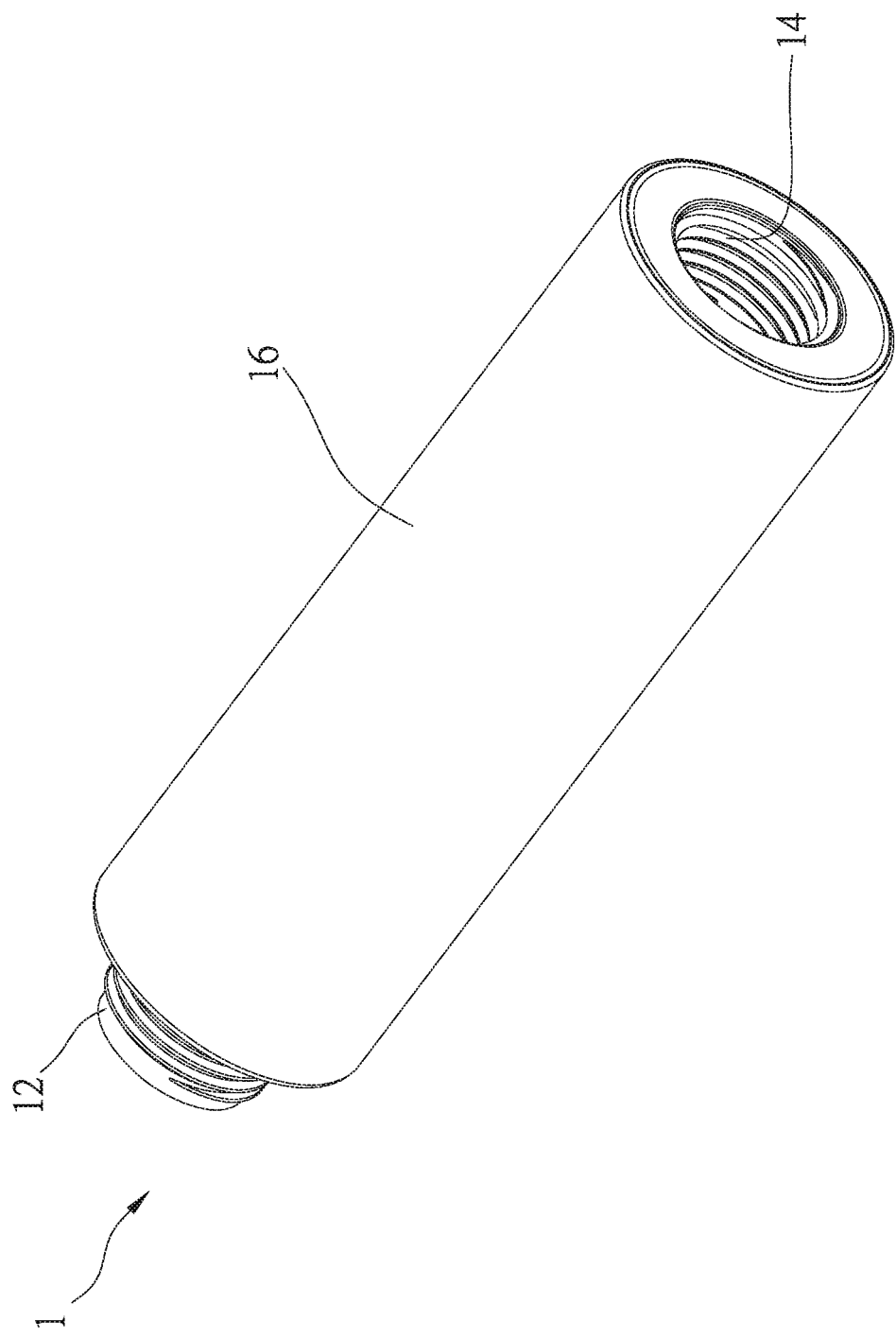
FIG. 1 is a perspective view of a UV sterilization tube of a first embodiment of the present disclosure.
Figure 2:
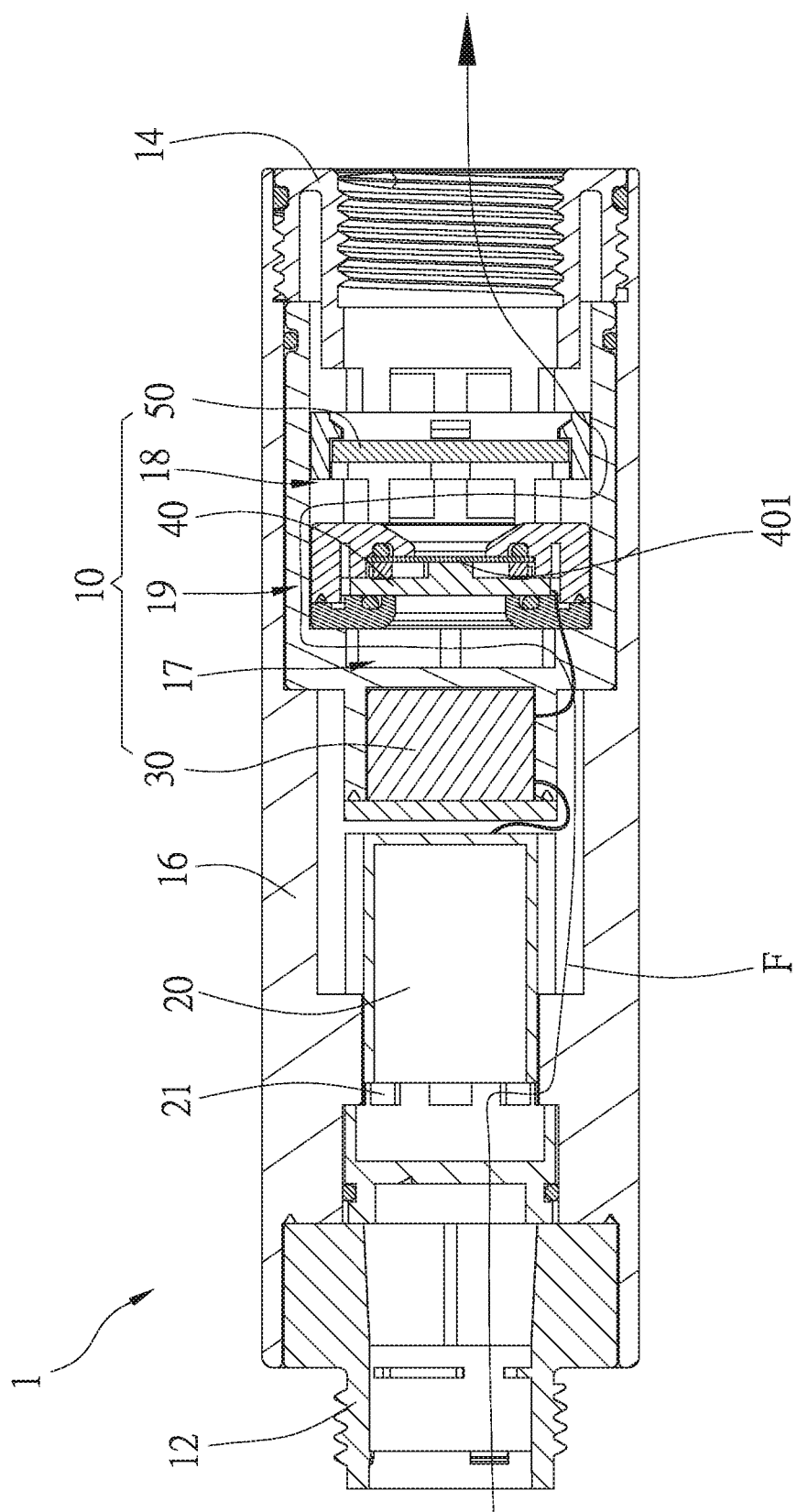
FIG. 2 is a cross-sectional view of the UV sterilization tube of the first embodiment of the present disclosure.
Figure 3:
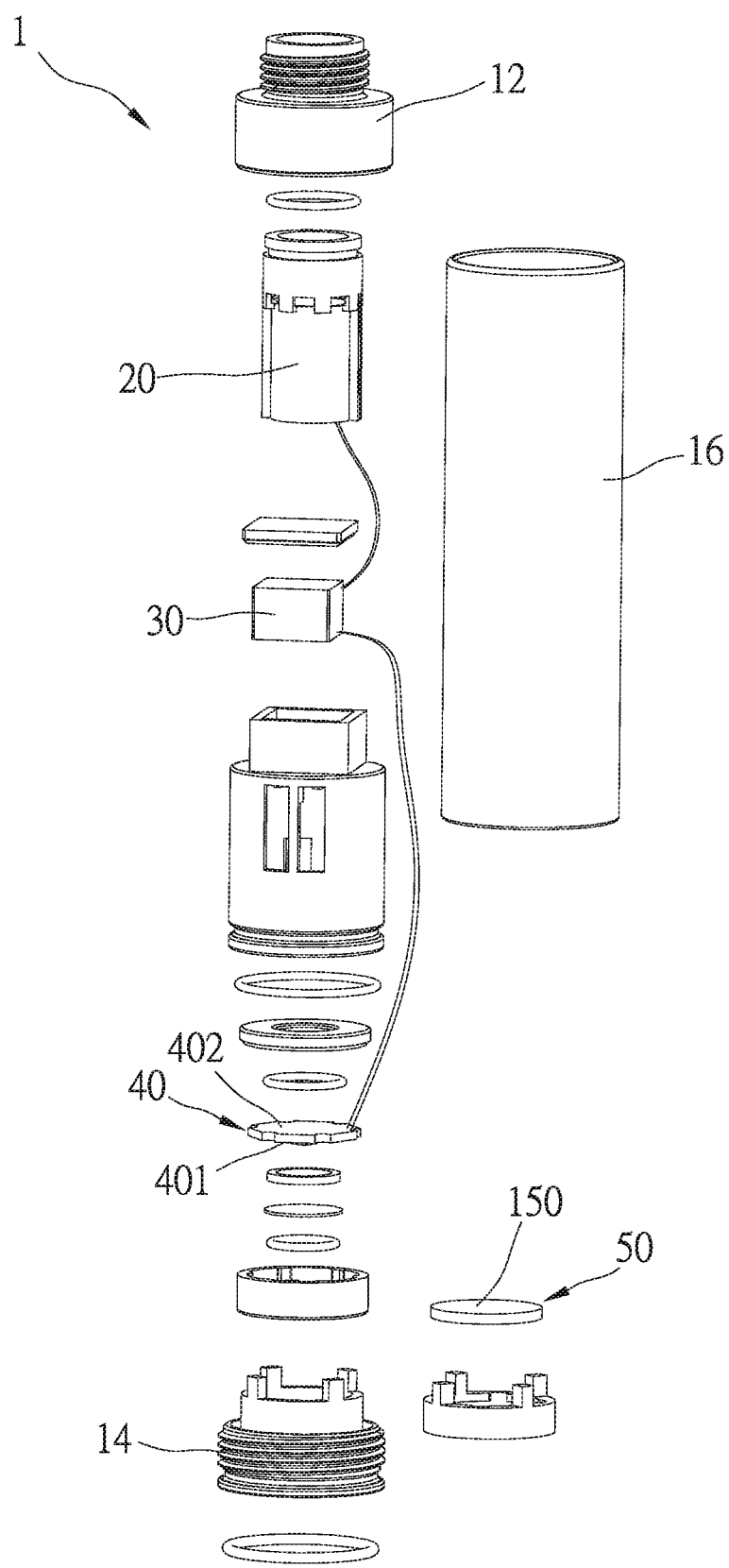
FIG. 3 is an exploded view of the UV sterilization tube of the first embodiment of the present disclosure.

As illustrated in FIG. 1 to FIG. 3, a UV sterilization tube 1 of the first embodiment of the present invention is provided. The UV sterilization tube 1 includes a hollow tube 16, a hydroelectric power module 20 and a UV sterilization module 10. The hollow tube 16 includes an inlet end 12 and an outlet end 14 communicating with each other. The hydroelectric power module 20 is positioned in the hollow tube 16, and communicates with the inlet end 12 and the outlet end 14 of the hollow tube 16, wherein the hydroelectric power module 20 generates electric power by a water flow F.

The UV sterilization module 10 is positioned in the hollow tube 16, and is electrically connected to the hydroelectric power module 20. The UV sterilization module 10 includes a UV source 40 and a reflector 50, wherein the UV source 40 has a light-emitting surface 401 facing to the reflector 50. According to one embodiments of the present invention, a sterilization channel 18 is between the UV source 40 and the reflector 50, and the sterilization channel 18 communicates with the inlet end 12 and the outlet end 14 of the hollow tube 16. According to one embodiments of the present invention, the reflector 50 has a reflection surface 501 facing to the light-emitting surface 401 of the UV source 40.

The UV sterilization module 10 includes an electronic control member 30. The electronic control member 30 is electrically connected to the hydroelectric power module 20 and the UV source 40. According to one embodiments of the present invention, the UV source 40 has an electrical connection surface 402 which is electrically connected to the electronic control member 30. According to one embodiments of the present invention, a cooling channel 17 is between the electrical connection surface 402 of the UV source 40 and the electronic control member 30, the cooling channel 17 communicates with the inlet end 12 and the outlet end 14. According to one embodiments of the present invention, the cooling channel 17 is used to cool down the UV source 40 while the UV source 40 is emitting UV light, which would increase the temperature of the UV source 40.

As shown in FIG. 2, the water flow F flows through the cooling channel 17 and the sterilization channel 18. It is worthy to note that, the water flow F does not flow between the hydroelectric power module 20 and the electronic control member 30.

According to one embodiments of the present invention, one end of the cooling channel 17 is connected to the inlet end 12 of the hollow tube 16, and another end thereof is connected to the sterilization channel 18; further, one end of the sterilization channel 18 is connected to the outlet end 14 of the hollow tube 16, and another end thereof is connected to the cooling channel 17.

According to another one embodiments of the present invention, one end of the sterilization channel 18 could be connected to the inlet end 12 of the hollow tube 16, and another end thereof is connected to the cooling channel 17; further, one end of the cooling channel 17 could be connected to the outlet end 14 of the hollow tube 16, and another end thereof is connected to the sterilization channel 18.

As shown in FIG. 2, the cooling channel 17 and the sterilization channel 18 are connected to form a zigzag flow route. According to one embodiments of the present invention, the cooling channel 17 and the sterilization channel 18 are substantially parallel to each other, and the cooling channel 17 is connected to the sterilization channel 18 through a side channel 19. According to one embodiments of the present invention, since the cooling channel 17 and the sterilization channel 18 are connected to form a zigzag flow route, the flow rate of the water flow F would be slow down, whereby the water would slow flow through the sterilization channel 18, in order to make water to be thoroughly sterilized and disinfected.

Referring to FIG. 3, the electrical connected surface 402 and the light-emitting surface 401 of the UV light source 40 are positioned on different sides. According to one embodiments of the present invention, the electrical connected surface 402 and the light-emitting surface 401 of the UV light source 40 are positioned back-to-back. As shown in FIG. 2 and FIG. 3, the electrical connected surface 402 of the UV light source 40 faces to the electronic control member 30.

As shown in FIG. 2, the electronic control member 30 is positioned between the hydroelectric power module 20 and the UV source 40. According to one embodiments of the present invention, the UV source 40 is positioned between the electronic control member 30 and the reflector 50. According to one embodiments of the present invention, the hydroelectric power module 20 is positioned between the UV sterilization module 10 and the inlet end 12. According to one embodiments of the present invention, the hydroelectric power module 20 has a water-driven blade assembly 21 facing to the inlet end 12, whereby the water flow F may drive the water-driven blade assembly 21 to rotate.

In practice, the hydroelectric power module 20 could be positioned between the UV sterilization module 10 and the outlet end 14. According to another one embodiments of the present invention, the hydroelectric power module 20 has a water-driven blade assembly 21 positioned back-to-back to the outlet end 14, whereby the water flow F may drive the water-driven blade assembly 21 to rotate.

As illustrated in FIG. 4 to FIG. 7, FIG. 10 and FIG. 11, a UV sterilization device 6 of the second embodiment of the present invention is provided. The UV sterilization device 6 includes a body 60, a power module 70 and a UV sterilization assembly 80. The body 60 includes a housing 62, an inlet end 64 and an outlet end 66. The inlet end 64 and the outlet end 66 are positioned on the housing 62 and communicate with the housing 62. The inlet end 64 and an outlet end 66 communicate with each other through the housing 62.

The power module 70 is positioned on the body 60 for supply electric power. According to embodiments of the present invention, the power module 70 is operably removed from the housing 62 of the body 60, whereby the power module 70 could be easily removed to change a new one. The power module 70 includes primary batteries, secondary batteries, mains electricity, a hydroelectric power module or combinations thereof.

The UV sterilization assembly 80 is positioned in the body 60, and is electrically connected to the power module 70. The UV sterilization assembly 80 includes a UV source 82 and at least one reflector 84, wherein the UV source 82 could emit UV light to the at least one reflector 84. According to embodiments of the present invention, the UV source 82 and the at least one reflector 84 are positioned around a sterilization channel 622 of the housing 62, and the sterilization channel 622 communicates with the inlet end 64 and the outlet end 66 of the body 60. According to embodiments of the present invention, the UV source 82 is operably removed from the housing 62 of the body 60, whereby the UV source 82 could be easily removed to change a new one.

Figure 7:
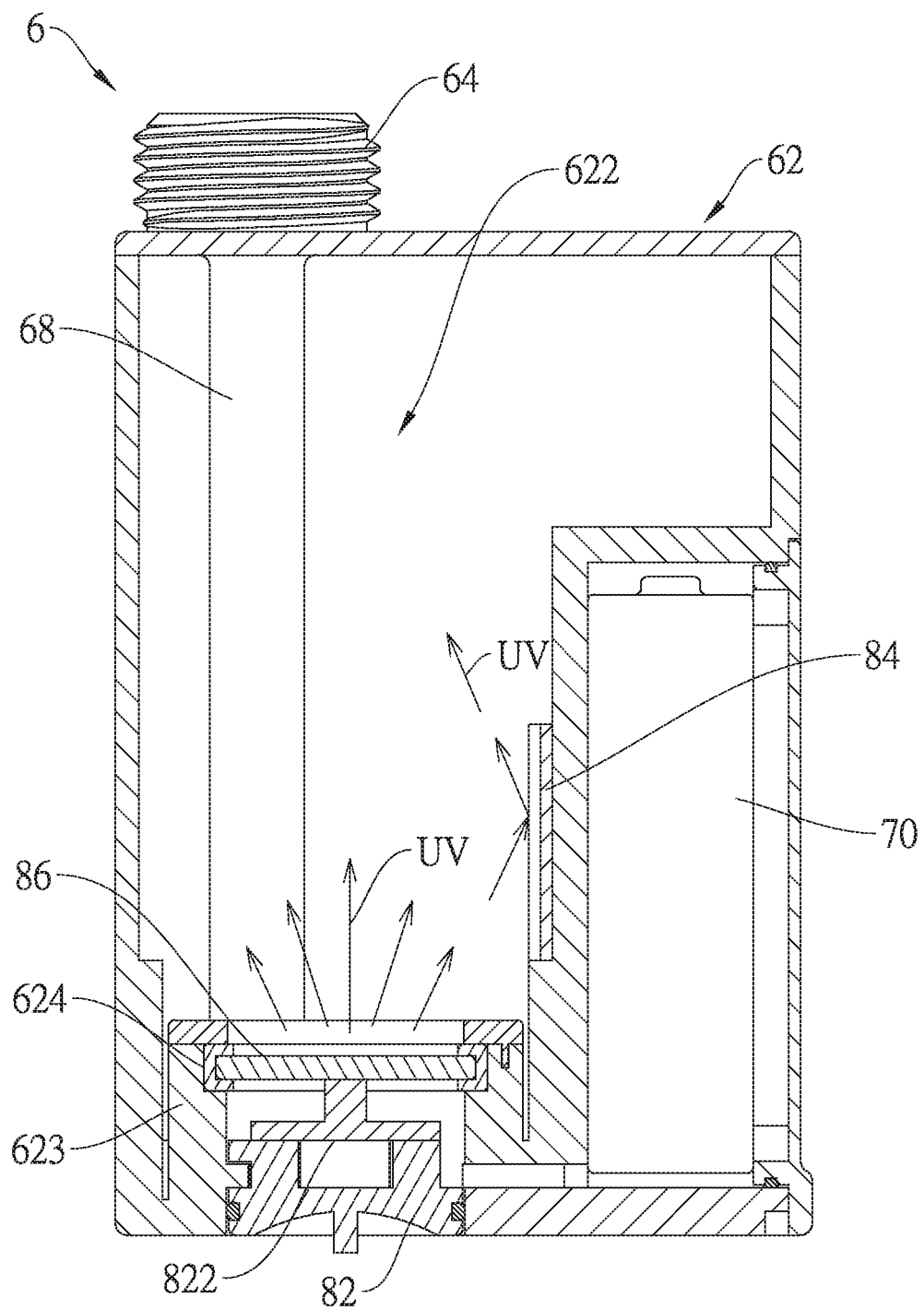
FIG. 7 is a cross-sectional view of the UV sterilization device of the second embodiment of the present disclosure taken along line 7-7.

Please referring to FIG. 7, the body 60 includes an inlet channel 68 and an outlet channel 69, the inlet channel 68 and the outlet channel 69 are positioned in the housing 62. The inlet end 64 communicates with the inlet channel 68, and the outlet end 66 communicates with the outlet channel 69. The sterilization channel 622 is positioned between the inlet channel 68 and the outlet channel 69, and communicates with the inlet channel 68 and the outlet channel 69. According to embodiments of the present invention, the inlet channel 68, the outlet channel 69 and the sterilization channel 622 are connected to form a zigzag water W flow route in the housing 62.

Figure 4:
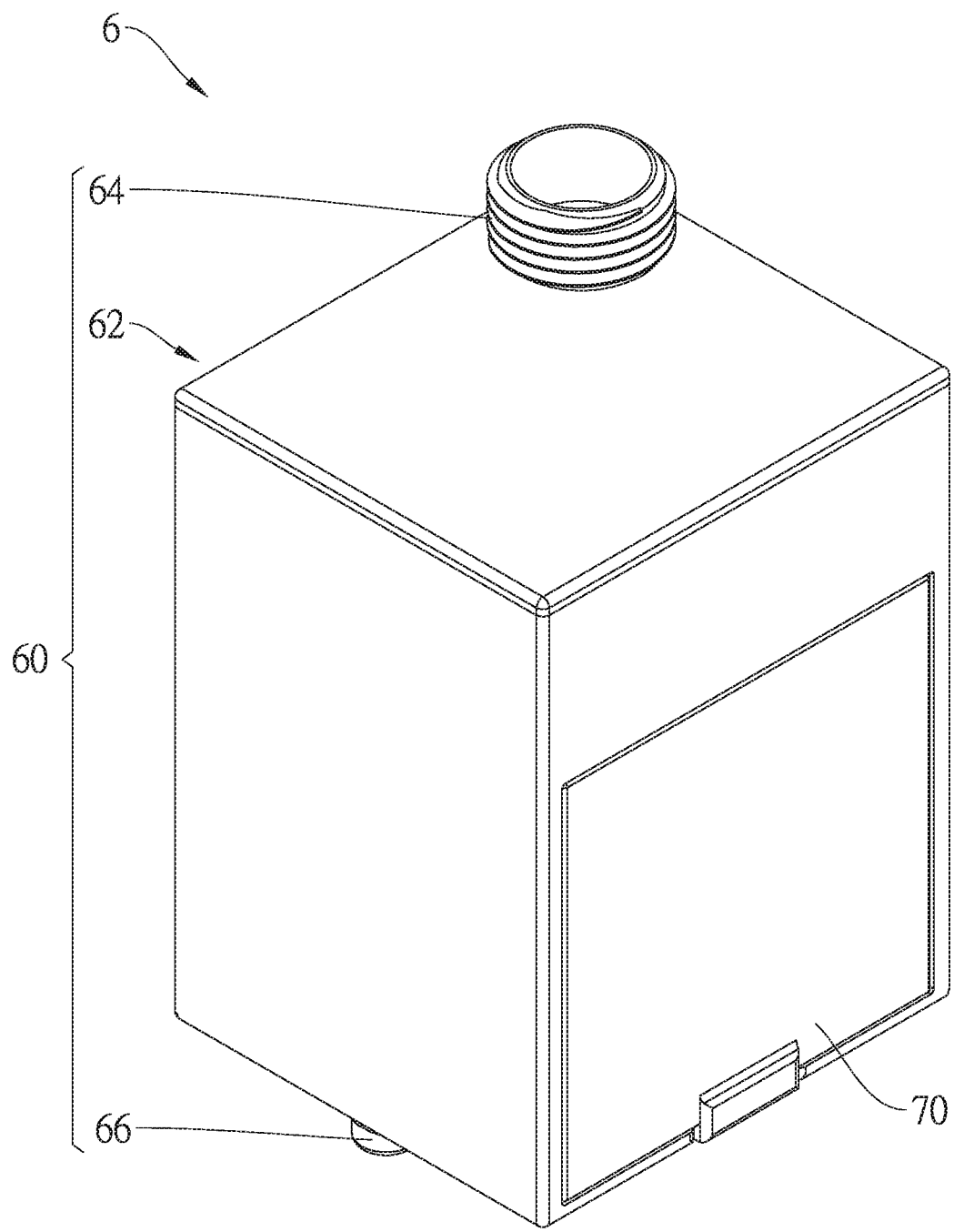
FIG. 4 is a perspective view of a UV sterilization device of a second embodiment of the present disclosure.

Please referring to FIG. 4, the housing 62 has a through hole 624 on a wall. The UV sterilization assembly 80 includes a transparent member 86, and the transparent member 86 is positioned on the wall 623 of the housing 62, and the through hole 624 is sealed by the transparent member 86.

The UV source 82 has a light-emitting surface 822 facing to the transparent member 86, and the UV light emitted from the UV source 82 passes through the transparent member 86 to illuminate the sterilization channel 622.

Figure 5:
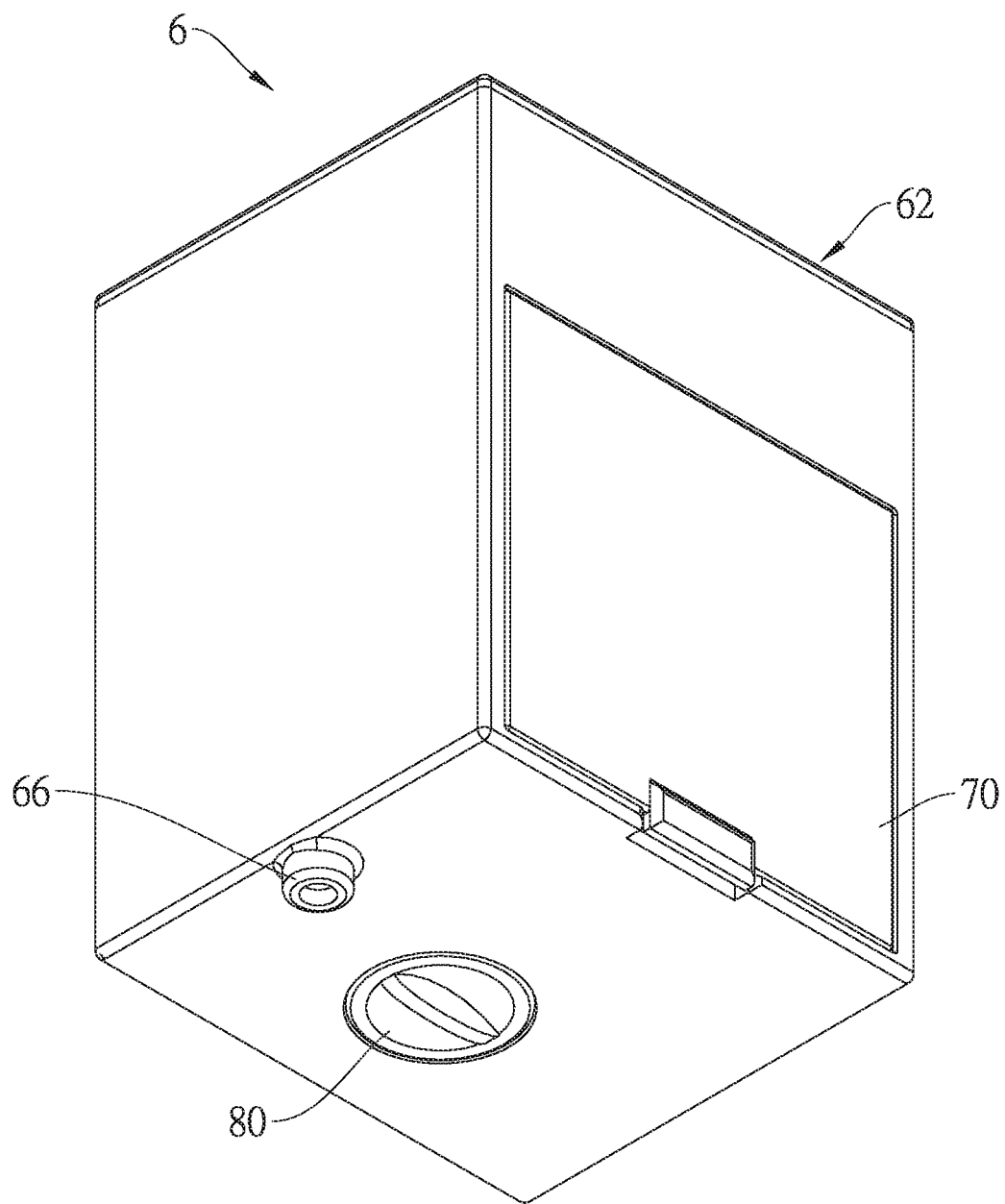
FIG. 5 is another perspective view of the UV sterilization device of the second embodiment of the present disclosure.
Figure 6:
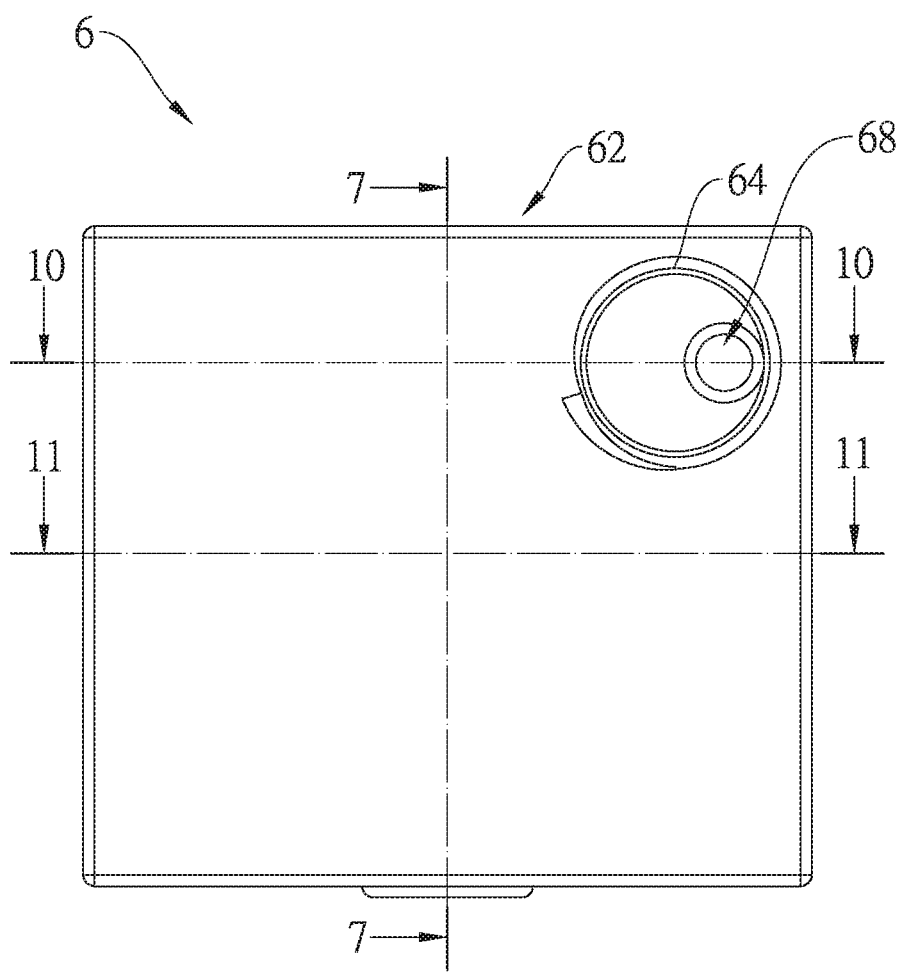
FIG. 6 is a top view of the UV sterilization device of the second embodiment of the present disclosure.

In FIG. 4 to FIG. 6, the at least one reflector 84 is positioned in the housing 62 around the sterilization channel 622. When the UV source 82 emits the UV light, the UV light is reflected by the at least one reflector 84 to illuminate the sterilization channel 622, in order to increase the sterilization efficiency of the UV sterilization device 6, 6A, 6B. According to embodiments of the present invention, the at least one reflector 84 is positioned on an inner wall of the housing 62.

In FIG. 5, the amount of the at least one reflector 84 is two or more, the reflectors 84 are individually positioned on inner walls of the housing 62. Each of the reflectors 84 has a reflection surface 842. The reflection surface 842 of one of the reflectors 84 faces to the reflection surface 842 of another one of the reflectors 84, in order to increase the sterilization efficiency of the UV sterilization device 6A.

In FIG. 6, the at least one reflector 84 has a reflection surface 842 facing to the light-emitting surface 822 of the UV source 82, in order to increase the sterilization efficiency of the UV sterilization device 6B.

Figure 8:
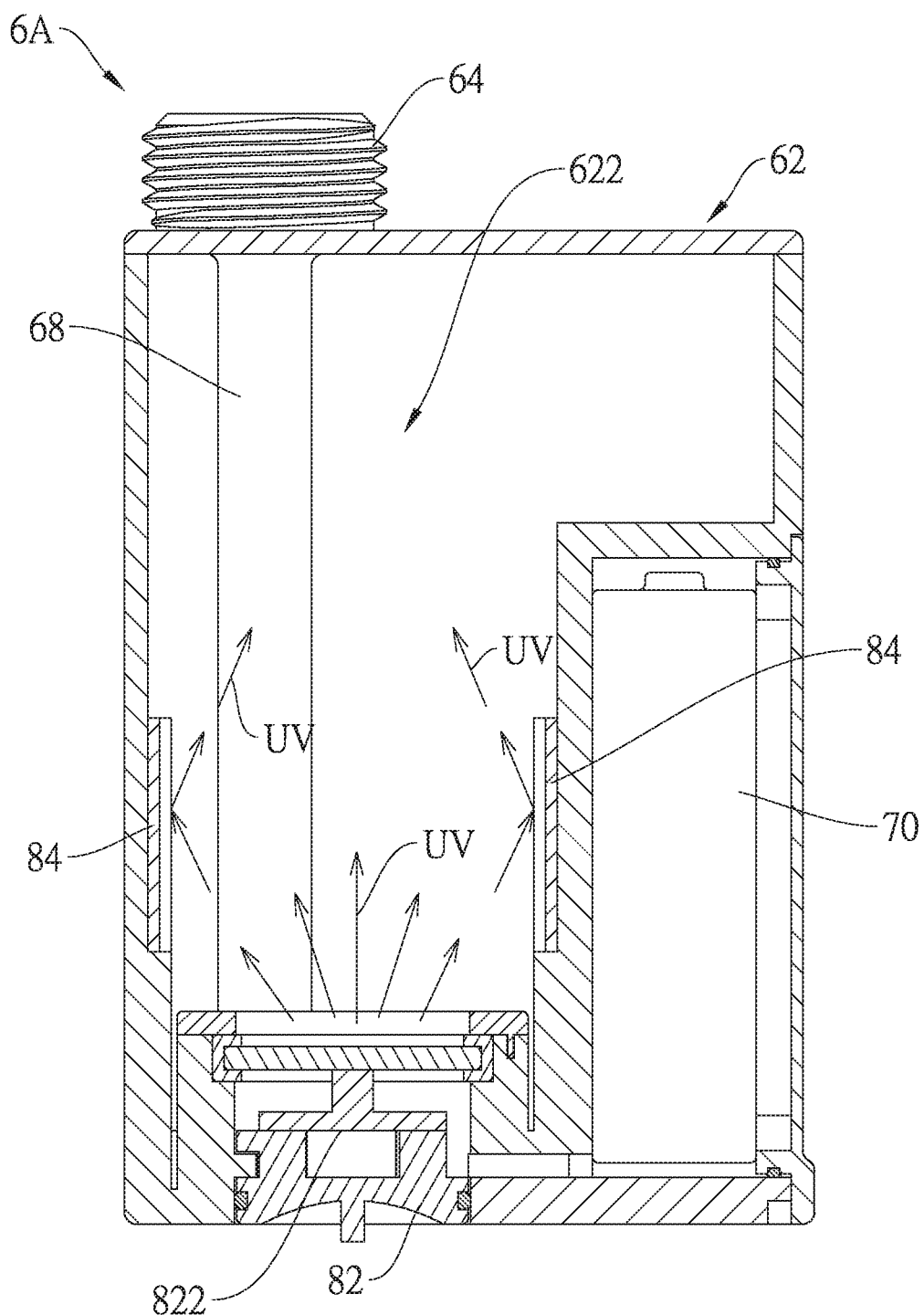
FIG. 8 is a cross-sectional view of another UV sterilization device of one embodiment of the present disclosure.

Please referring to FIG. 7 and FIG. 8, the inlet channel 68 has an inner diameter which is less than or equals to that of the inlet end 64, and the outlet channel 69 has an inner diameter which is greater than or equals to that of the outlet end 66. It is worthy to mention that, the body 60 could further include a check valve 67 positioned in the outlet channel 69 to prevent backward flow of water W. The check valve 67 could prevent water W already flow through the inlet channel 68 and the sterilization channel 622 from draining back down into the outlet channel 69 and the sterilization channel 622 when the water faucet shuts off.

Figure 9:
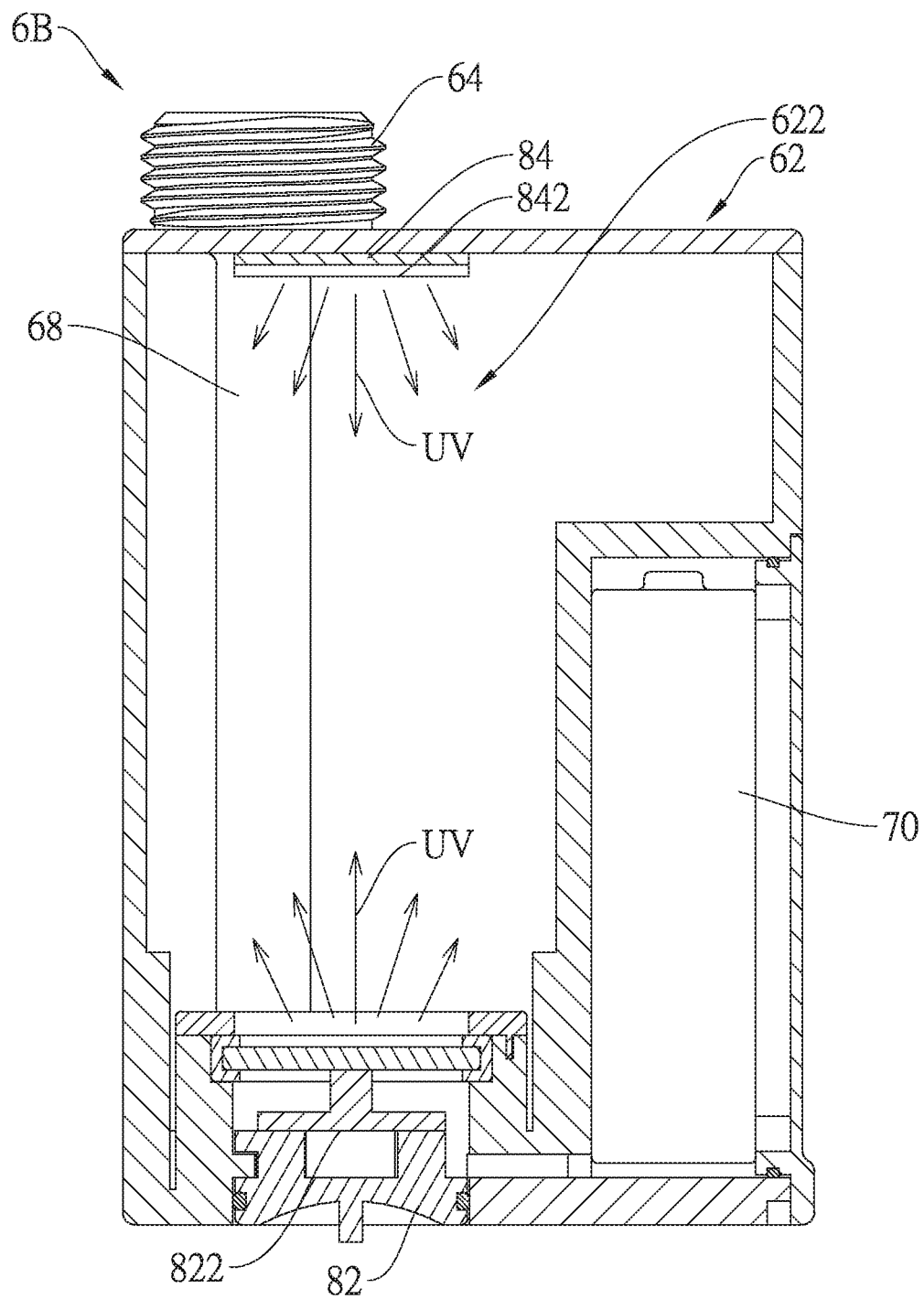
FIG. 9 is a cross-sectional view of another UV sterilization device of one embodiment of the present disclosure.
Figure 10:
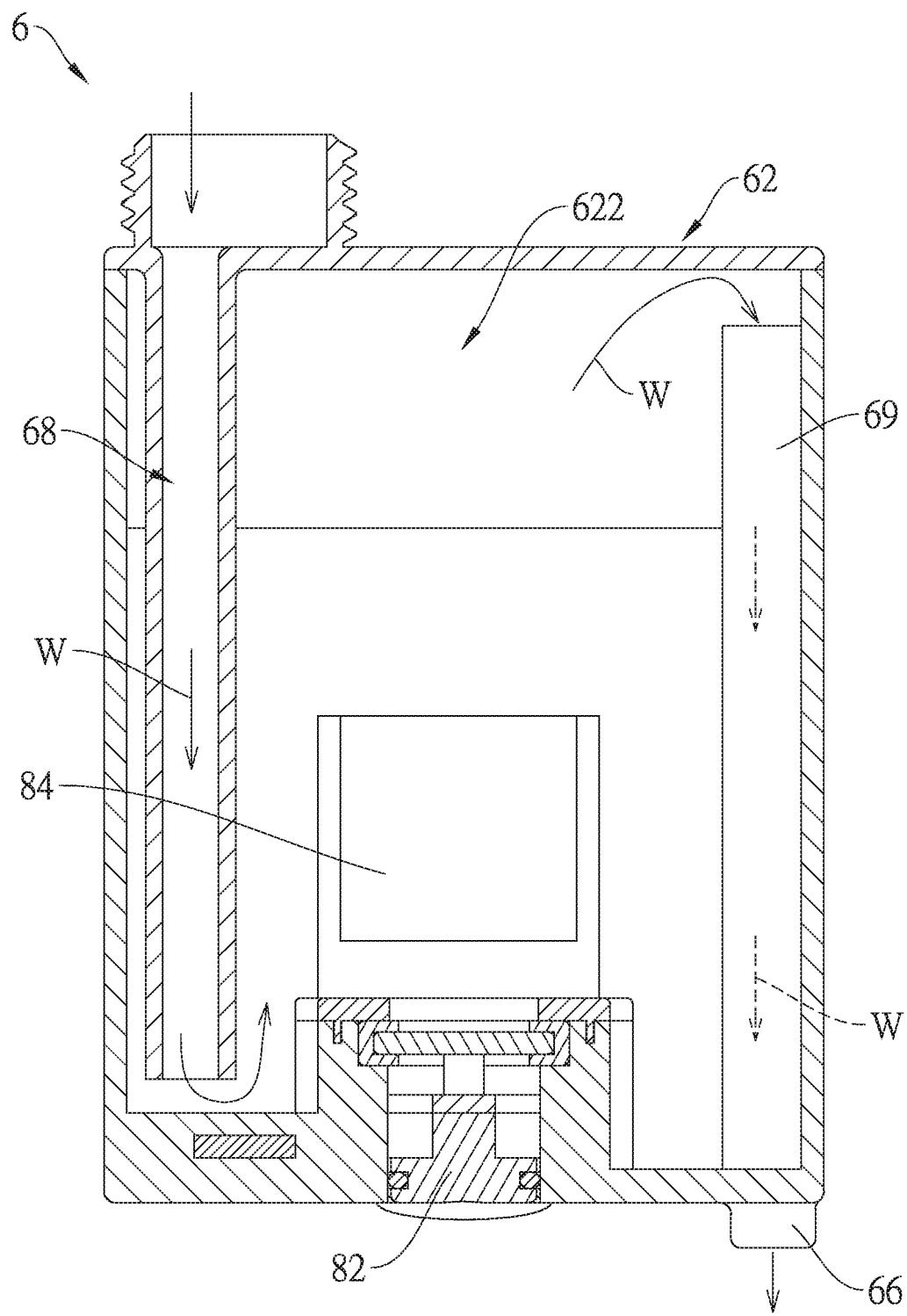
FIG. 10 is another cross-sectional view of the UV sterilization device of the second embodiment of the present disclosure taken along line 10-10.
Figure 11:
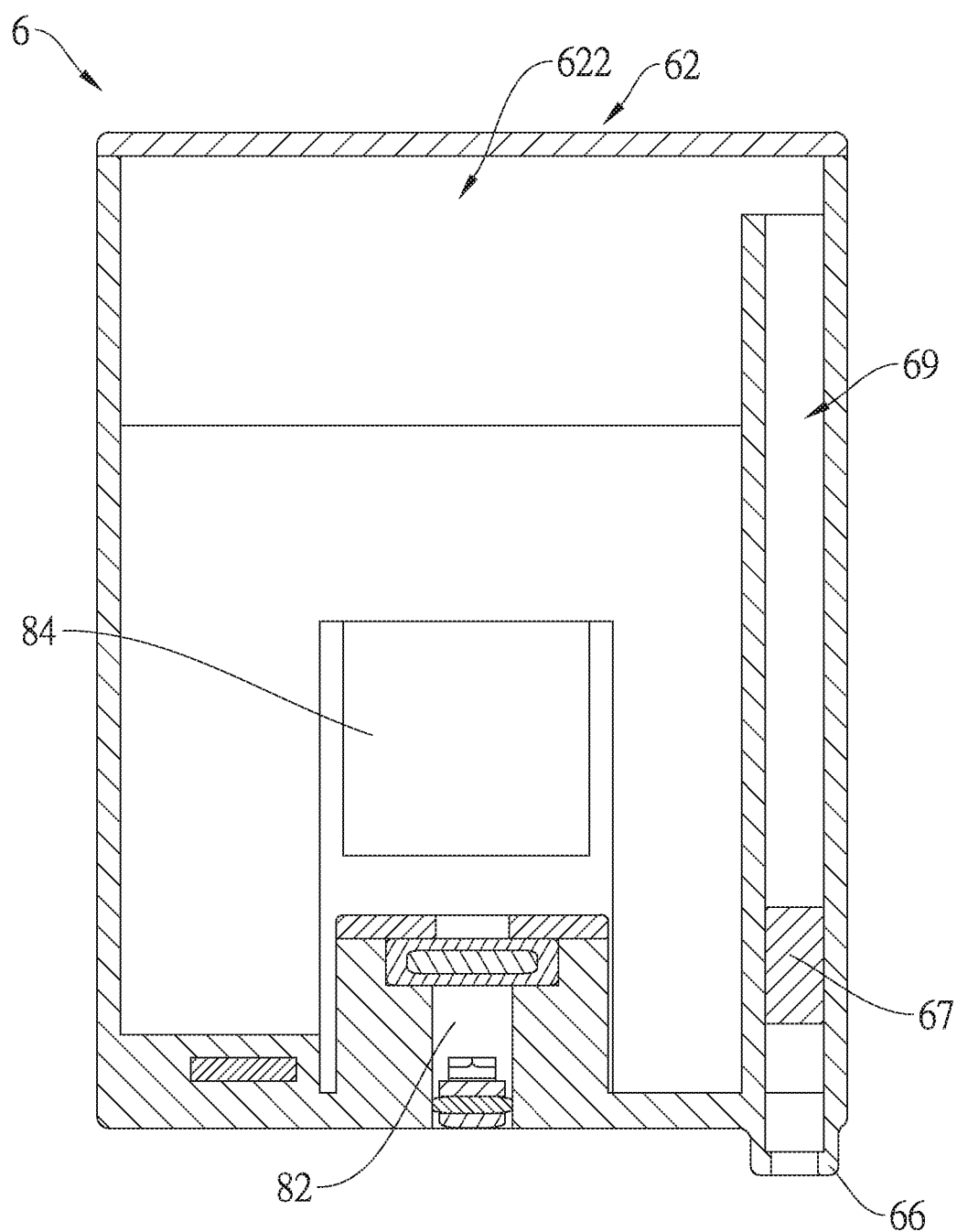
FIG. 11 is another cross-sectional view of the UV sterilization device of the second embodiment of the present disclosure taken along line 11-11.
Figure 12:
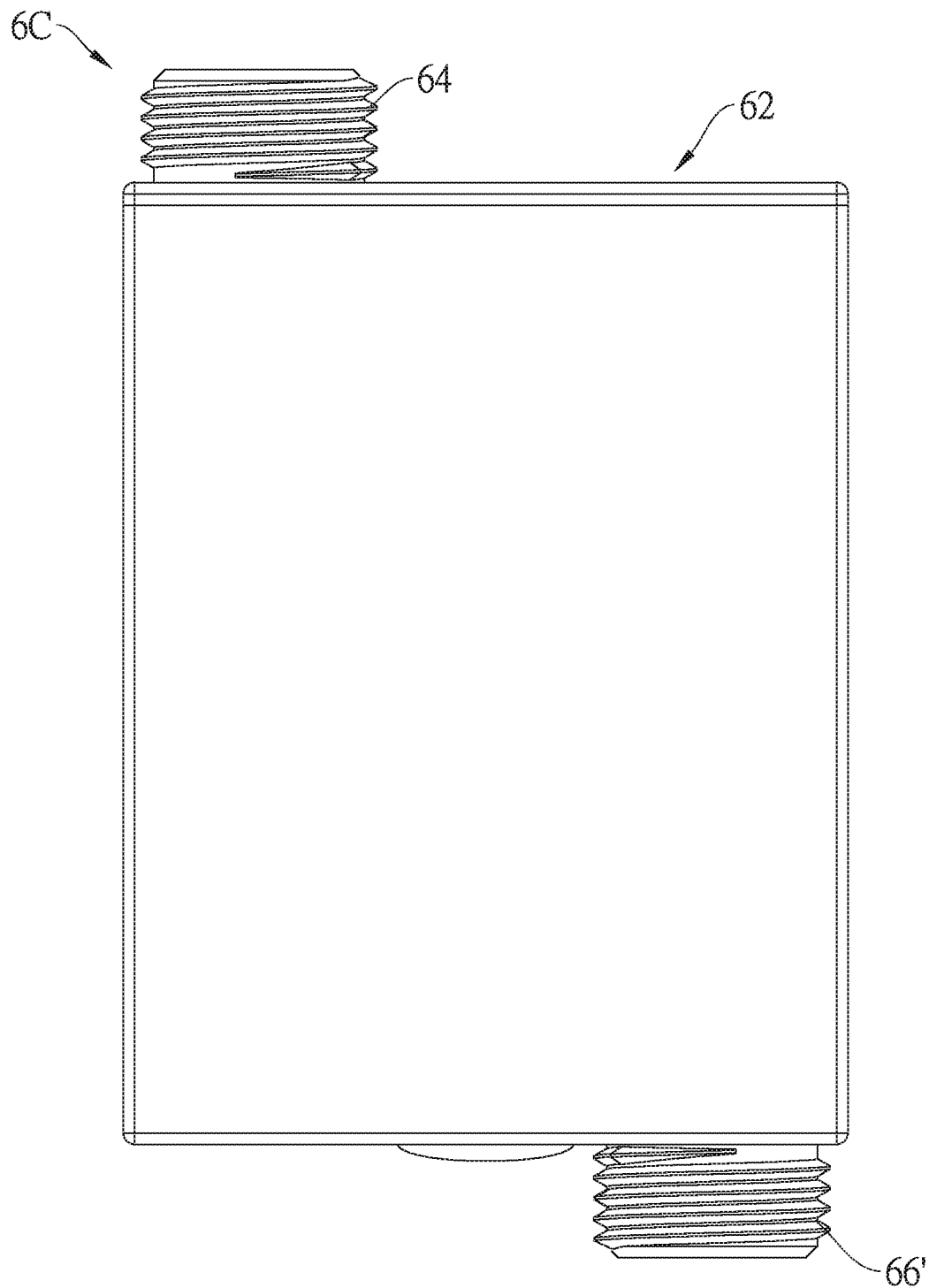
FIG. 12 is a side view of another UV sterilization device of one embodiment of the present disclosure.

Please referring to FIG. 9, the outlet end 66 of the UV sterilization device 6C is different from that of the UV sterilization device 6. In FIG. 9, the outlet end 66 is the same as the inlet end 64, so that the UV sterilization device 6C is easily installed with regular size water pipes.

With the aforementioned design, the UV sterilization device includes a power module which could supply electric power, whereby to provide the electric power to the UV sterilization assembly. Thereby, the UV sterilization device provided in the present invention has a slim size, so that there is no need to make an enough space to install the UV sterilization device.

It must be pointed out that the embodiments described above are only some preferred embodiments of the present disclosure. All equivalent structures which employ the concepts disclosed in this specification and the appended claims should fall within the scope of the present disclosure.

What is claimed is:

1. A UV sterilization device, comprising:
a body, comprising a housing, an inlet end and an outlet end, wherein the inlet end and the outlet end are positioned on the housing and communicate with the housing; the inlet end and an outlet end communicate with each other through the housing;
a power module, positioned on the body for supply electric power;
a UV sterilization assembly, positioned on the body, and electrically connected to the power module, the UV sterilization assembly comprises a UV source and at least one reflector, wherein the UV source could emit UV light to the at least one reflector, and the UV source and the at least one reflector are positioned around a sterilization channel, the sterilization channel communicates with the inlet end and the outlet end of the body;
wherein the body comprises an inlet channel and an outlet channel, the inlet channel and the outlet channel are positioned in the housing; the inlet end communicates with the inlet channel, and the outlet end communicates with the outlet channel; the sterilization channel is positioned between the inlet channel and the outlet channel, and communicates with the inlet channel and the outlet channel;
wherein the body comprises a check valve positioned in the outlet channel to prevent backward flow of water.

2. The UV sterilization device of claim 1, wherein the inlet channel, the outlet channel and the sterilization channel are connected to form a zigzag flow route in the housing.

3. The UV sterilization device of claim 1, wherein the inlet channel has an inner diameter which is less than or equals to an diameter of the inlet end; the outlet channel has an inner diameter which is greater than or equals to an diameter of the outlet end.

4. The UV sterilization device of claim 1, wherein the housing has a through hole on a wall; the UV sterilization assembly comprises a transparent member, the transparent member is positioned on the wall of the housing, and the through hole is sealed by the transparent member.

5. The UV sterilization device of claim 4, wherein the UV source has a light-emitting surface facing to the transparent member, and the UV light emitted from the UV source passes through the transparent member to illuminate the sterilization channel.

6. The UV sterilization device of claim 1, wherein the UV source is operably removed from the body.

7. The UV sterilization device of claim 1, wherein the at least one reflector is positioned in the housing around the sterilization channel; when the UV source emits the UV light, the UV light is reflected by the at least one reflector to illuminate the sterilization channel.

8. The UV sterilization device of claim 7, wherein the at least one reflector is positioned on an inner wall of the housing.

9. The UV sterilization device of claim 8, wherein the at least one reflector has a reflection surface facing to the light-emitting surface of the UV source.

10. The UV sterilization device of claim 7, wherein the amount of the at least one reflector is two or more, the reflectors are individually positioned on inner walls of the housing; each of the reflectors has a reflection surface; the reflection surface of one of the reflectors faces to the reflection surface of another one of the reflectors.

11. The UV sterilization device of claim 1, wherein the power module is operably removed from the body.

12. The UV sterilization device of claim 1, wherein the power module comprises primary batteries, secondary batteries, mains electricity, a hydroelectric power module or combinations thereof.

* * * * *